US00PP07898P

United States Patent [19]

van Andel

[11] Patent Number: Plant 7,898

[45] Date of Patent: Jun. 30, 1992

[54] CARNATION NAMED STAYELPA

[75] Inventor: Jacob van Andel, Aalsmeer, Netherlands

[73] Assignee: Va Staaveren B.V., Netherlands

[21] Appl. No.: 604,528

[22] Filed: Oct. 29, 1990

[51] Int. Cl.[5] ..... A01H 5/00

[52] U.S. Cl. ..... Plt./70

[58] Field of Search ..... Plt./70, 71

*Primary Examiner*—James R. Feyrer

*Attorney, Agent, or Firm*—Charles W. Rummler

[57] ABSTRACT

A new and original carnation cultivar particularly distinguished by its large, Dresden-yellow blossoms, which are produced continuously throughout the Spring, Summer, Fall, and Winter blooming periods on a plant which has a strong and vigorous growth habit and a height of about 80 cm.

1 Drawing Sheet

BACKGROUND OF THE NEW PLANT

This new carnation cultivar as a Hybrid Seedling developed by me in 1985 at our nursery in Aalsmeer, Holland by crossing two varieties selected from our collection of carnations maintained for breeding purposes at Aalsmeer. This particular seedling was selected for propagation because of its large, Dresden-yellow flowers, which grow well even under low light intensity, and the overall high quality of its growth habit. Asexual propagation of this selected plant was done by means of cuttings under my direction at Aalsmeer and propagation of this new plant continued from generation to generation to determine whether the novel characteristics of the selected seedling would hold true from generation to generation so that its homogeneity could be assured.

This proved to be successful and this new carnation variety is now being propagated at Aalsmeer.

DESCRIPTION OF THE DRAWING

My new carnation cultivar is illustrated by the accompanying photographic drawing, which shows blooming portions of flower stems with the flowers shown in full development, the color rendition being as nearly true to that herein specified as is reasonably possible to obtain by professional photographic procedures.

DECRIPTION OF THE NEW PLANT

The following is a detailed description of my new carnation variety based upon observation of plants grown in greenhouse as well as outdoors at Aalsmeer and blooming during the current year. The color designations stated herein are according to The R.H.S. COLOUR CHART published by The Royal Horticultural Society of London, England.

THE PLANT

Origin: Seedling.

Parentage:

*Seed parent.*—84230-1B (unpatented).

*Pollen parent.*—Londorga U.S. Plant Pat. No. 5,784.

Classification:

*Botanic.*—*Dianthus Caryophyllus.*

*Commercial.*—Standard carnation.

Form: Tall, vigorous bush.

Height: 80 cm, in average.

Main stem:

*Length.*—About 80 cm.

*Growth.*—Vigorous and strong.

*Branching character.*—One side shoot at each node.

Foliage:

*Number of leaves.*—Varies with season or the amount of daylight.

*Leaf size.*—13.5×1.0 cm at the fifth node.

*Leaf shape.*—Pointed and slightly curled. Margins: Entire. Texture: Leathery. Color: Both upper and under side are gray-green.

THE BUD

Size: Medium.

*Diameter.*—Averaging about 2 cm.

*Length.*—Averaging about 3 cm.

Shape: Columnar.

Calyx:

*Shape.*—Columnar.

*Size.*—Averaging about 17 mm in width and 30 mm in length.

*Splitting.*—The calyx does not split.

*Aspect.*—Smooth.

Flower stem:

*Character.*—Erect.

*Color.*—Gray-green.

*Length.*—Approximately 70–80 cm.

THE FLOWER

Blooming habit: Continuous, blooming the year round.

Size of flower: Large.

*Diameter.*—Averaging about 8 cm.

*Depth.*—Averaging about 4 cm.

Borne: Singly.

Shape:

*When first opening.*—High center.

*When mature.*—Somewhat flattened, high center.

Petalage:

*Number of petals.*—Approximately 30–35.

*Texture.*—Soft.

*Appearance.*—Velvety.

*Arrangement.*—Imbricated.

*Form/shape.*—Ovate.

*Margin type.*—Deeply serrate.

*Color.*—Both outer and inside petals: Body: 5 C/D. Base: 5 C/D. Reverse side: 5 C/D. Red flecks appear on the petals, along with inconspicuous white striations of the outer petals.

Flower stem:

*Character.*—Strong and upright.

Discoloration:

*After full bloom.*—No discoloration.

Persistence: The flowers hang on and dry.

Diease resistance: Resistant of Fusarium Oxysporum.

Lasting quality: Averaging about 14 days as a cut flower and 21 days on the plant.

Fragrance: Slight.

REPRODUCTIVE ORGANS

Stamens:

*Number.*—Few — approximately 3–8.

*Arrangement.*—Petaloid.

*Anthers.*—Size: Small. Color: White.

*Filaments.*—Length: 35 mm, in average. Color: White.

*Pollen.*—Color: Yellow.

Pistils:

*Number.*—1.

*Styles.*—Length: 30 mm, in average. Color: White.

*Stigmas.*—Color: White with yellow shadings.

Characteristics of ovaries: Conical.

FRUIT

Fertility: The fruit is fertile.

Shape: Conical.

Color at maturity: Light brown.

I claim:

1. The new and distinctive carnation cultivar, substantially as herein shown and described, particularly characterized by its large, Dresden-yellow flowers, which are continuously blooming even under a low light intensity and are borne singly on strong, upright stems.

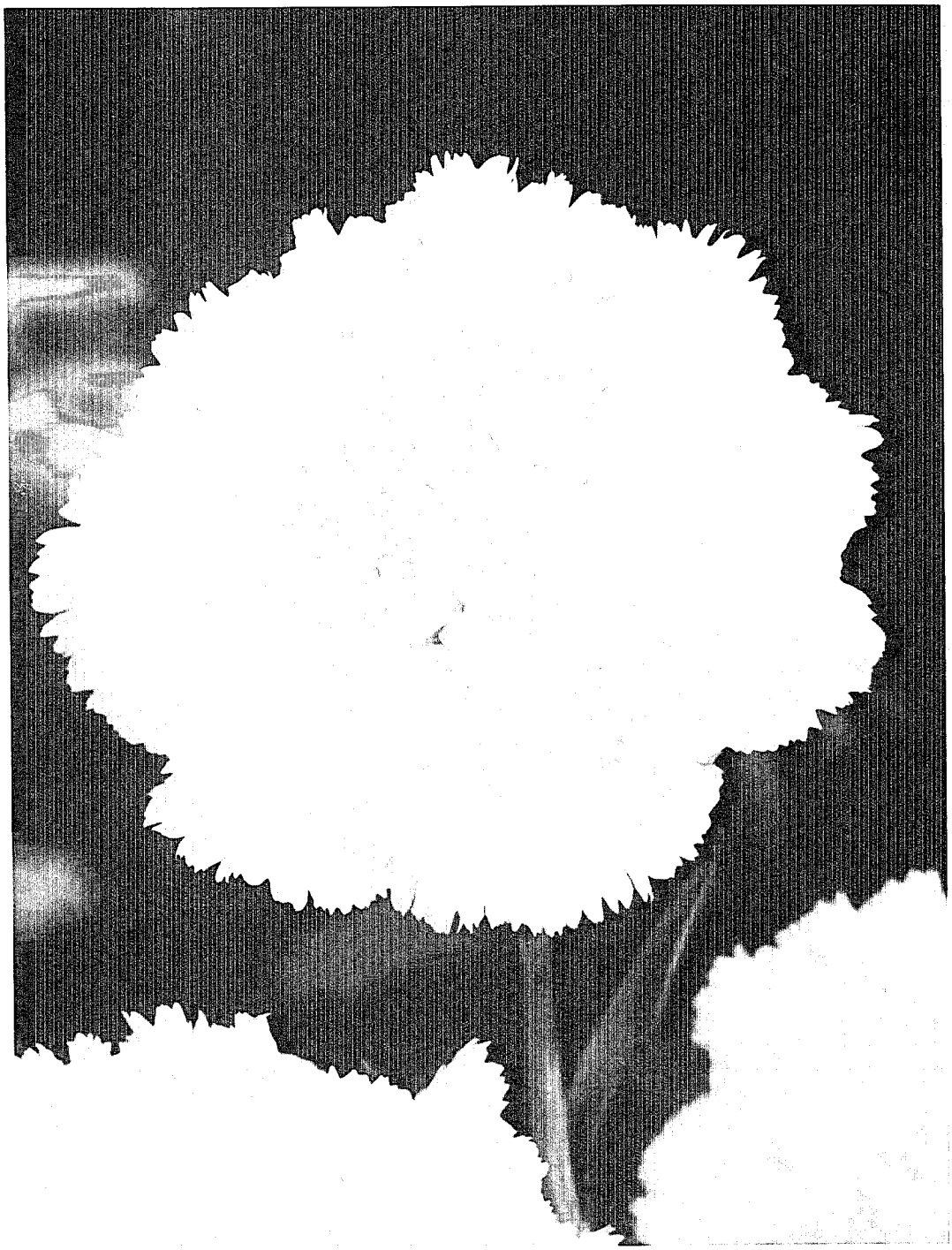

* * * * *